United States Patent [19]

Kurtz et al.

[11] 4,306,558

[45] Dec. 22, 1981

[54] PORTABLE LIQUID COLLECTION DEVICE

[75] Inventors: Leonard D. Kurtz, Woodmere; Robert E. Bidwell, Melville, both of N.Y.

[73] Assignee: Bioresearch Inc., Farmingdale, N.Y.

[21] Appl. No.: 119,784

[22] Filed: Feb. 8, 1980

[51] Int. Cl.³ .............................................. A61M 1/00
[52] U.S. Cl. ..................................... 128/276; 15/353; 15/327 R
[58] Field of Search ............... 128/276, 277, 278, 297, 128/760, 765, 353, 327 R, 327 A, 327 F; 15/327 A, 327 F, 353, 327 D, 327 R, 341, 344, 335, 351; 137/205; D15/52, 55

[56] References Cited

U.S. PATENT DOCUMENTS

| | | | |
|---|---|---|---|
| 1,292,963 | 1/1919 | Replogle | 15/335 |
| 2,230,264 | 2/1941 | Replogle | 15/335 |
| 2,989,769 | 6/1961 | Houser | 15/353 |
| 3,267,510 | 8/1966 | Cote | 15/344 |

FOREIGN PATENT DOCUMENTS 571706 9/1945 United Kingdom ................ 128/276

Primary Examiner—Robert W. Michell
Assistant Examiner—J. L. Kruter
Attorney, Agent, or Firm—Larson and Taylor

[57] ABSTRACT

A portable liquid collection device is disclosed which is used for draining the pleural cavity or the like. An electric pump and battery means are located inside of a housing. Also located inside of the housing are an adjustable valve and a manually operated emergency pump. A detachable liquid collection chamber is held to the housing by a handle and a latch on the handle. Extending from the pump to the collection chamber through the handle is a vacuum line. When a hose from the pleural cavity is connected to the collection chamber, the electric pump is turned on by a switch and creates a vacuum in the chamber which draws liquids through the hose. If liquid in the chamber rises too high, a float valve in the chamber prevents any liquid from being drawn into the vacuum line.

9 Claims, 3 Drawing Figures

PORTABLE LIQUID COLLECTION DEVICE

FIELD OF THE INVENTION

This invention relates generally to devices for draining an area of fluids by creating a vacuum in a collection chamber, and more particularly to a portable device which has an integral detachable collection chamber.

BACKGROUND OF THE INVENTION

Whenever extraneous fluids are introduced into the body's cavities or passages, it is necessary that these fluids be drained before they accumulate. For example, following a surgical incision through the rib case in order to perform surgery on the lung, or following stab or bullet wounds which pierce the rib cage, fluids such as water, blood, or air may be deposited in the pleural cavity. If such fluids are allowed to accumulate in the pleural cavity, breathing becomes difficult and ultimately impossible. Therefore it is imperative that any fluids which are deposited in this cavity be removed quickly.

In order to withdraw fluids from the body, a tube is usually connected at one end to the cavity to be drained and at the other end to a source of vacuum or suction. Usually the tube is first connected to a chamber which is maintained at a vacuum so that the fluid is collected in the chamber.

While a stationary source of vacuum may be readily available in a hospital, there are many times when a movable source is needed, for example, at the site of an accident or wounding and while the patient is being transported to a hospital. In addition, a portable source of vacuum may be used in a hospital after surgery when a patient is being moved to the recovery room. In some cases, it may even be desireable to provide an ambulatory patient with such a device to enable him to carry it with him wherever he goes.

SUMMARY OF THE INVENTION

In accordance with the present invention, a self-contained, portable fluid collection device is provided for draining fluids from a body cavity or the like. An integral detachable collection chamber is provided with connection means for a hose so that the fluids withdrawn from the body through the hose are collected in the chamber. The chamber is maintained at a vacuum by an electric pump powered by batteries located in the device. An emergency pump which is manually operable is also provided in case of failure of the electric pump. In order to adjust the vacuum in the chamber, a bleed valve is provided along with a vacuum gauge to indicate the degree of vacuum. To protect the electric motor from damage by the collected liquids, a float valve is located in the collection chamber to cut off flow to the pump from the chamber when the liquids rise too high.

Additional features and advantages of the present invention are stated in or apparent from the detailed description of a presently preferred embodiment found hereinbelow.

DETAILED DESCRIPTION OF THE PREFERRED EMBODIMENTS

Figure 1:
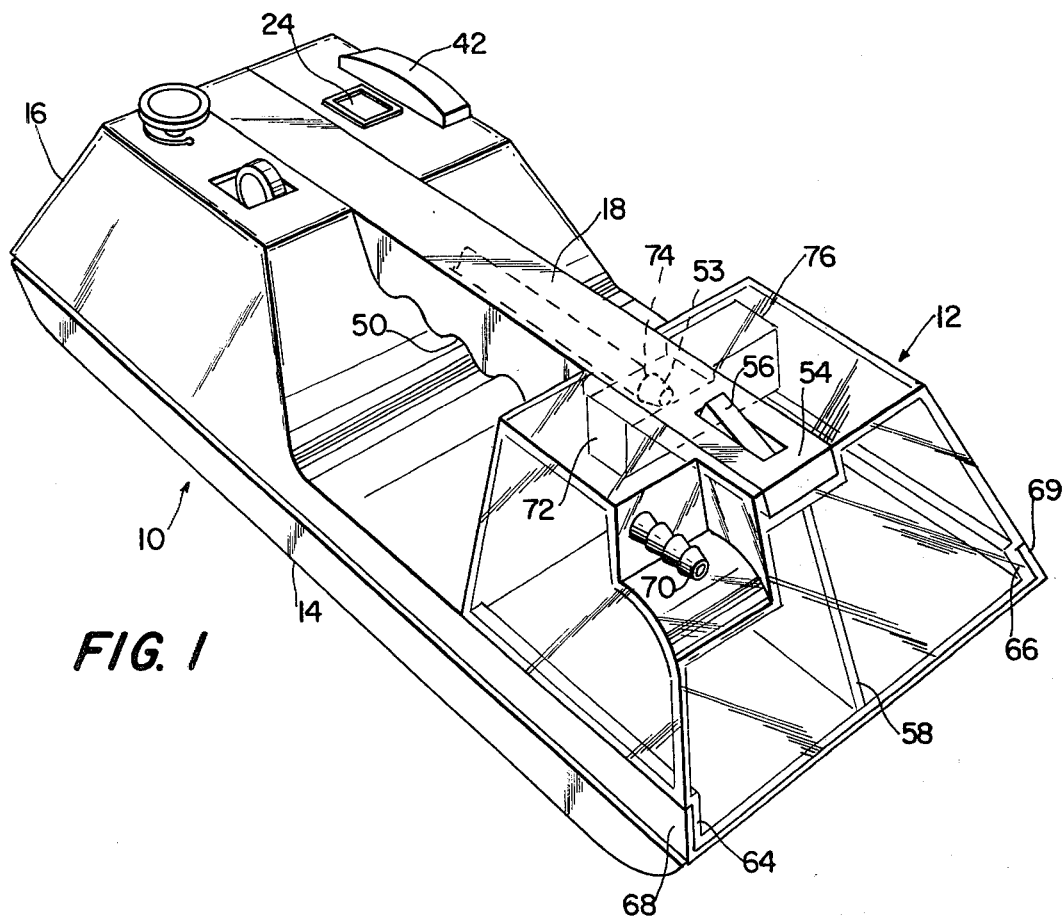
FIG. 1 is a perspective view of a preferred embodiment of the portable fluid collection device of the present invention.
Figure 3:
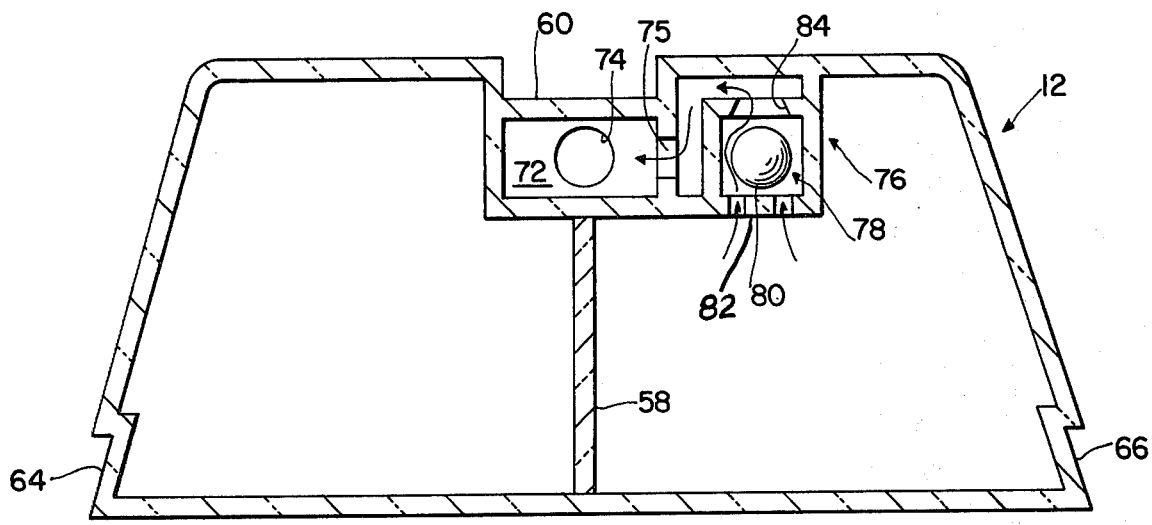
FIG. 3 is a cross-sectional view of the detachable collection chamber taken along the line 3—3 in FIG. 2.
Figure 2:
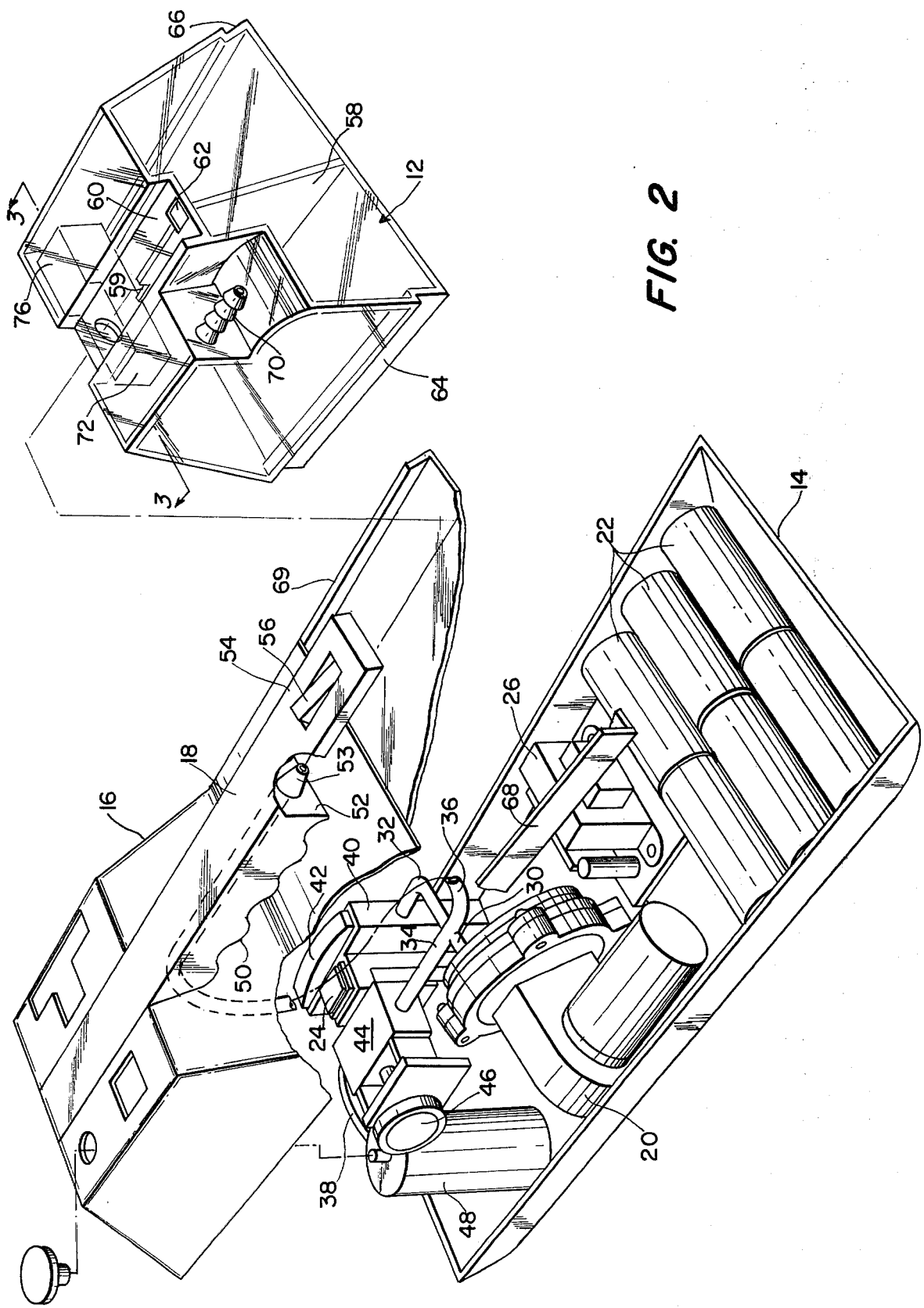
FIG. 2 is an exploded perspective view of the device depicted in FIG. 1.

With reference now to the drawings in which like numerals represent like elements throughout the several views, a presently preferred embodiment of the present invention is depicted in FIGS. 1 and 2 and comprises a housing 10 and a detachable collection chamber 12. Housing 10 consists of a base 14 and a top 16 having a handle 18. Located inside of housing 10 and attached to base 14 is a suitable dc electric pump 20. Electric pump 20 is electrically connected to a set of batteries 22 through an on-off switch 24 by suitable wires (not shown). Also electrically connected to batteries 22 is a battery recharger 26 which is adapted to be easily connected to a standard source of electric current.

Electric pump 20 sucks air from a tube 30 towards pump 20, creating a partial vacuum in tube 30. Tube 30 joins tubes 32, 34 and 36 so that a corresponding vacuum is created in each of these tubes. Tube 32 leads to vacuum gauge 40 having a meter which is read through an indicating window 42 extending through top 16. In order to control the degree of vacuum, tube 34 is connected to a bleed valve 44. The amount of air which is bled into tube 34 through bleed valve 44 is adjusted by means of a knob 46. A tube 38 extends from bleed valve 44 to a manually operated pump 48. Lastly, tube 36 extends through handle 18 into detachable collection chamber 12.

As can be seen in FIG. 2, handle 18 protrudes from housing 10 and has a scalloped portion 50 to facilitate carrying of the device by hand. At the end of scalloped portion 50 handle 18 has a flat face forming a stop 52. Tube 36 extends slightly beyond the face of stop 52 and ends in a conically shaped portion 53. Beyond stop 52, handle 18 is reduced in cross-section and this forms a guide 54. Near the end of guide 54 is a resiliently mounted latch 56 which extends slightly below the bottom face of guide 54.

Detachable collection chamber 12 is preferably formed of semi-transparent plastic so that the fluid level inside of it can be seen. To make it easier to judge the accumulation of liquids in chamber 12, the interior area is divided into two halves by an interior wall 58. At the top of wall 58 an opening 59 is provided so that after liquids have accumulated in one side the liquids then spill over to the other side. A slot 60 along the top of chamber 12 has a shape corresponding to guide 54 so that guide 54 slides in slot 60. Near the end of slot 60, a notch is cut to form a catch 62 for the end of latch 56. The side walls 64 and 66 of chamber 12 are inwardly directed so that they form a trapezoidal shape. Base 14 of housing 12 has a pair of correspondingly inwardly shaped flanges 68 and 69 which slidably receive side walls 64 and 66. A hose connector 70 extends from chamber 12 to which a hose running to the area to be drained is attached.

Located below slot 60 inside of chamber 12 is a compartment 72 having a vacuum line opening 74 at the back. Another opening 75 in compartment 72 leads to a valve compartment 76. Inside of valve compartment 76 is a float valve 78 having a float ball 80 between an apertured bottom 82 in fluid communication with the interior of chamber 12 and a ball seat 84 located above float ball 80.

In operation, the portable fluid collection device functions in the following manner. When the portable fluid collection device is needed, a detachable collection chamber 12 is removed from its sterile packaging and attached to housing 10. Detachable collection chamber 12 slides onto housing 10 as guide 54 of handle 18 slides in slot 60 of chamber 12 and side walls 64 and 66 of chamber 12 slide between flanges 68 and 69 of base 14. As the back wall of chamber 12 reaches stop 52 on handle 18, conical end portion 53 of vacuum line 36 extending slightly beyond stop 52 is received snugly inside of vacuum line opening 74. At the same time that chamber 12 hits stop 52, latch 56 engages catch 62 to hold chamber 12 securely on housing 10.

After connecting the hose from the drainage site to hose connector 70, the device is ready to operate. Switch 24 is then used to provide power to electric pump 20. Electric pump 20 is powered by batteries 22 and a vacuum is thereby created in tube 30. This vacuum is transmitted to detachable collection chamber 12 by tube 36 and ultimately to the drainage site. In order to control the degree of vacuum in detachable collection chamber 12, bleed valve 44 is adjusted by knob 46 to bleed air into tube 34 and through pump 20. Vacuum gauge 40, which is attached to tube 30 by tube 32, shows the degree of vacuum through the meter in indicating window 42.

After operation for a period of time, it is possible that detachable collection chamber 12 might become filled with liquid. If this liquid were allowed to travel through tubes 36 and 30 into pump 20, serious damage to pump 20 might result. To prevent this from occuring, float valve 78 functions in the following manner. As the liquid level rises in detachable collection chamber 12, the liquid enters valve compartment 76 through apertured bottom 82. Float ball 78 which is in valve compartment 76 floats on top of the liquid. When the liquid rises high enough, float ball 78 seats on ball seat 84. This closes the connection between the collection chamber and the vacuum line and thus prevents liquid from passing into the vacuum line. At this time, or preferably before this stage is reached, latch 56 is depressed and detachable collection chamber 12 is removed from housing 12 to be replaced with a new sterilized detachable collection chamber 12.

Should electric pump 20 fail for any reason, for example through breakdown or through the batteries becoming discharged, an emergency pump 48 is manually operable to maintain a vacuum in detachable collection chamber 12. Manually operated pump 48 is connected to detachable collection chamber 12 through tube 38, bleed valve 44, and tubes 34 and 36.

By providing battery recharger 26, it is possible to use rechargeable batteries to power the device and to thus keep the batteries at approximate full charge. Battery recharger 26 is a well-known device in the art and it is adapted to receive a standard plug from a standard house current. The rechargeable batteries can be recharged whether electric pump 20 is operating or not, and thus the device can operate even on weak batteries so long as recharger 26 is connected to a source of electricity.

Although the invention has been described in detail with respect to an exemplary embodiment thereof, it will be understood by those of ordinary skill in the art that variations and modifications may be effected within the scope and spirit of the invention.

We claim:

1. A portable fluid collection device comprising a housing including an outwardly extending base portion to receive a collection chamber, pump means in said housing, a vacuum line connected to said pump means, a hollow integrally mounted handle on said housing, said handle having a free end extending from said housing above the base portion, said vacuum line extending through said handle, a collection chamber separate and detachable from said base portion of the housing, a groove formed in said collection chamber to receive the free end of said handle when said collection chamber is attached to said housing, an opening in said collection chamber adapted to be in alignment with said vacuum line when the collection chamber is received on the handle of said housing, latch means for latching the collection chamber to the handle and to secure said housing and collection chamber together, means for collecting said collection chamber with a body cavity of a patient whereby when said device is operative, said pump means maintains a lowered pressure in the collection chamber and in the body cavity of the patient and the collection chamber receives fluid from the body cavity and when the collection chamber is filled, the collection chamber may be removed from the housing.

2. A portable fluid collection device as claimed in claim 1, further including a second pump means located in said housing and fluidly connected to said vacuum line such that said second pump means is used as a backup for said pump means.

3. A portable fluid collection device as claimed in claim 1, further including a valve means for preventing fluid collected in said collection chamber from entering said pump means.

4. A portable fluid collection device as claimed in claim 1, further including means for adjusting the degree of vacuum maintained in said collection chamber.

5. A portable fluid collection device comprising:

a housing;

a battery located in said housing;

a vacuum producing electric pump electrically connected to said battery and located in said housing;

a handle protruding from said housing and located above a portion of said housing;

latch means including a stop on said handle;

a vacuum line extending from said electric pump, through said handle, and having a portion which terminates beyond said stop of said handle;

an adjustable bleed valve fluidly connected to said vacuum line and located in said housing;

a manually operated emergency pump which is fluidly connected to said bleed valve;

a detachable liquid collection chamber;

means for connecting said chamber with a hose leading to the area to be drained;

a vacuum line opening in said chamber which receives the portion of said vacuum line extending beyond said stop of said handle;

a valve means located between said means for connecting a hose and said vacuum opening for preventing the withdrawal of any liquid through said vacuum line; and a recessed slot in said collection chamber for receiving said reduced end portion of said handle;

such that said chamber is held between said handle and said housing by said latch means and as said chamber slides onto said housing and said handle, said handle acts as a guide in said recessed slot of said chamber so that said vacuum line opening receives the portion of said vacuum line extending beyond said stop.

6. A portable fluid collection device as claimed in claim 5, wherein said valve means is a float valve fluidly connected to said vacuum line and having an apertured compartment containing a float and a float seat located in said chamber at a level such that as the liquid level in said chamber rises to an undesired height, the liquid enters said compartment and causes said float to press against said float seat thus cutting off the flow of any liquid from said chamber through said vacuum line.

7. A portable fluid collection device as claimed in claim 5 further comprising a battery recharging means located in said housing which is electrically connected to said battery and which is adapted to be connected to a standard current source so that said batteries are recharged.

8. A portable fluid collection device as claimed in claim 5 further comprising a vacuum gauge located in said housing which is fluidly connected to said vacuum line so that the amount of suction existing in said vacuum line is detected.

9. A portable fluid collection device as claimed in claim 5 wherein the sides of said chamber are inwardly directed and said housing includes a pair of upstanding flanges which are similarly inwardly directed so that the sides of said chamber are slidably recessed between said flanges.

* * * * *